United States Patent [19]

Sherwin

[11] Patent Number: 4,631,466
[45] Date of Patent: Dec. 23, 1986

[54] PHASE LOCKED STEPPER MOTOR CONTROLLED LIGHT CHOPPER

[75] Inventor: Gary W. Sherwin, South Huntingdon Township, Westmoreland County, Pa.

[73] Assignee: Westinghouse Electric Corp., Pittsburgh, Pa.

[21] Appl. No.: 727,156

[22] Filed: Apr. 25, 1985

[51] Int. Cl.$^4$ ............................................. H02P 8/00
[52] U.S. Cl. ..................................... 318/696; 318/685
[58] Field of Search ................ 318/696, 685; 250/233; 358/42

[56] References Cited

U.S. PATENT DOCUMENTS

| | | | |
|---|---|---|---|
| 3,435,213 | 3/1969 | Colbow et al. | 250/233 |
| 4,145,644 | 3/1979 | Lin | 318/696 |
| 4,272,712 | 6/1981 | Beling et al. | 318/696 |
| 4,523,224 | 6/1985 | Longacre, Jr. | 358/42 |

Primary Examiner—William M. Shoop, Jr.
Assistant Examiner—Saul M. Bergmann
Attorney, Agent, or Firm—Daniel C. Abeles

[57] ABSTRACT

A phase locked loop stepper motor controlled light chopper for providing a specific pattern reversal rate. The stepper motor controlled light chopper includes a phase comparator for comparing the phase of a reference signal to the phase of a comparison signal; a RC low pass filter for filtering the output of the phase comparator; a voltage controlled oscillator having a frequency varying in response to the output of the RC filter. The chopper also includes a binary counter for generating count signals responsive to the frequency of the voltage controlled oscillator; a divide by 10 circuit counting one of the outputs of the binary counter and providing the comparison signal. The light chopper also includes a memory circuit for storing an eight state four bit gray code for driving a four phase stepper motor as a chopper wheel in a specified pattern mounted on a drive shaft.

6 Claims, 5 Drawing Figures

| B3 | B2 | B1 | | D3 | D2 | D1 | D0 |
|---|---|---|---|---|---|---|---|
| 0 | 0 | 0 | | 1 | 1 | 0 | 1 |
| 0 | 0 | 1 | | 1 | 0 | 0 | 1 |
| 0 | 1 | 0 | | 1 | 0 | 1 | 1 |
| 0 | 1 | 1 | | 1 | 0 | 1 | 0 |
| 1 | 0 | 0 | | 1 | 1 | 1 | 0 |
| 1 | 0 | 1 | | 0 | 1 | 1 | 0 |
| 1 | 1 | 0 | | 0 | 1 | 1 | 1 |
| 1 | 1 | 1 | | 0 | 1 | 0 | 1 |

PHASE LOCKED STEPPER MOTOR CONTROLLED LIGHT CHOPPER

CROSS REFERENCE TO RELATED APPLICATIONS

This application is related to concurrently filed, co-pending U.S. application entitled Evoked Potential Autorefractometry System by Bernard, Roth, Mohan, Sherwin and Zomp assigned to the assignee of the present invention and having U.S. Ser. No. 727,156.

BACKGROUND OF THE INVENTION

1. Field of the Invention

The present invention relates to mechanical light shutter systems in which a motor drives a shutter wheel at a precise frequency; and more particularly, to the motor drive system for such a mechanical light shutter system used in an evoked potential autorefractometry system.

2. Description of the Related Art

Many scientific experiments are based on the response of an observed system to light. In these experiments, it is highly desirable that the system be exposed to light in synchronism with measurements of the system's response to the light. One example of such a scientific experiment is the reaction of a human being's eyes to light. In such a system, the brain waves that a person generates when viewing particular scenes can be low level signals; thus, the light source/motor drive system must generate minimum noise. Additionally, when detecting the brain waves of a person viewing a particular scene, it is necessary that the particular scene be alternated at a rate of less than 7 hertz so that the brainwaves indicating perception of the alternating scene are of a frequency less than the typical low limit for alpha waves. Typically, scenes are reversed at rate of 6 Hz.

FIG. 1 schematically illustrates prior means utilized by the applicant to generate the required reversal of a scene while simultaneously attempting to minimize the amount of noise generated by the motor drive system.

Referring to FIG. 1A, the applicant initally chose an AC motor 10 to drive a chopper wheel 15. The chopper wheel 15 can have printed thereon the particular pattern that is to be reversed and observed by a person. While the AC motor has very desirable noise characteristics in that the noise level is constant and can thus be subtracted from any measurements of the observed system. However, the A.C. motor can only operate at one frequency and can not track the frequency of an external signal source. The inability to track an external signal source is a major drawback because, when measuring a person's response to a pattern reversal, the human eye also picks up, for example, the flickering of fluorescent lamps which occurs at rate being a multiple of the 60 Hz power line frequency. It is desirable, therefore, to sychronize the reversal rate of the particular pattern and thus the persons perception of the pattern to an external source such as the 60 Hz line frequency so that the noise due to the overhead fluorescent lamps can be removed from the measured signal.

FIG. 1B schematically illustrates a second device for providing a pattern reversal rate developed by the applicant. This second approach utilizes a DC motor 20 and provides the ability to vary the frequency at which the chopper wheel 15 rotates. This approach, as with the first approach, has the drawback that it cannot track an external signal source. An additional drawback of this approach is that the DC motor generates correlated non-constant amplitude noise due to the brushes of the motor sliding over the slots in the commutator. Because the amplitude of this noise is nonconstant, brain wave measurements indicating the persons response to the pattern being reversed cannot be adjusted for this noise.

To provide the ability to track an external source, the applicant next developed the system schematically illustrated in FIG. 1C. This system employs a phase lock loop (PLL) controlled DC motor 25, and provides both variable frequency drive of the chopper wheel 15, and the ability to track an external signal source. This system, however, generates correlated, nonconstant amplitude noise due to the brushes crossing the slots in the commutator, and therefore as in the FIG. 1B system, this noise cannot be subtracted from the measured brain waves.

To eliminate the correlated noise, the applicant next utilized a stepper motor 30 as shown in FIG. 1D. This system has the beneficial features of a variable frequency drive for the chopper wheel 15 and constant amplitude noise that was correlated to the motion of the motor, enabling the brain wave measurements to be compensated for this noise. The system, however, could not track an external signal source and thus, could not be synchronized to an external noise source such as fluorescent lamps.

SUMMARY OF THE INVENTION

It is an object of the present invention to provide a low noise variable frequency light chopper drive.

It is another object of the present invention to provide a low noise variable frequency chopper wheel drive that is capable of tracking an external signal source.

It is a further object of the present invention to provide a variable frequency motor drive capable of tracking an external signal source, and generating minimum noise such that the generated noise is synchronized to the movement of the motor and has a constant amplitude.

It is still a further object of the present invention to provide a phase locked loop motor control generating noise that is synchronized to the motion of the motor and has a constant amplitude.

It is still another object of the present invention to provide a phase locked loop control stepper motor for driving a light chopper.

Yet another object of the present invention is to provide a phase locked loop motor control suitable for use in an evoked potential autorefactometry system.

In a preferred embodiment of the present invention, a phase comparator circuit is connected to receive a reference signal and a comparison signal. The output of the phase comparator circuit is applied to a RC low pass filter whose output is then applied to a voltage controlled oscillator to generate a signal having a frequency varying in accordance with the output of the RC filter. A binary counter counts the transitions in the output of voltage controlled oscillator, and generates signals representing the number of transistions counted. The counter circuit counts the number of transistions in one of the signals generated by the binary counter, and after a predetermined number of these signals outputs a count signal corresponding to the comparison signal. A memory circuit receives the outputs of the binary counter and generates an eight (8) state gray code in accordance with the output of the binary counter. The output of the memory circuit drives a plurality of transistors which are connected to a stepper motor having a four (4) phase winding and a drive shaft with a chopper wheel mounted on it.

These together with other objects and advantages which will be subsequently apparent, reside in the details of construction and operation as more fully hereinafter described and claimed, reference being had to the accompanying drawings forming a part hereof, wherein like numerals refer to like parts throughout.

DETAILED DESCRIPTION OF THE PREFERRED EMBODIMENT

The present invention provides a phase locked stepper motor controlled light chopper with variable frequency chopper wheel drive and external signal source tracking capabilities. The noise produced by this system has a minimum constant amplitude and is synchronized with the motion of the motor so that the noise can be subtracted out of any measurements made on a system illuminated by passing through the chopper wheel.

Figure 1:
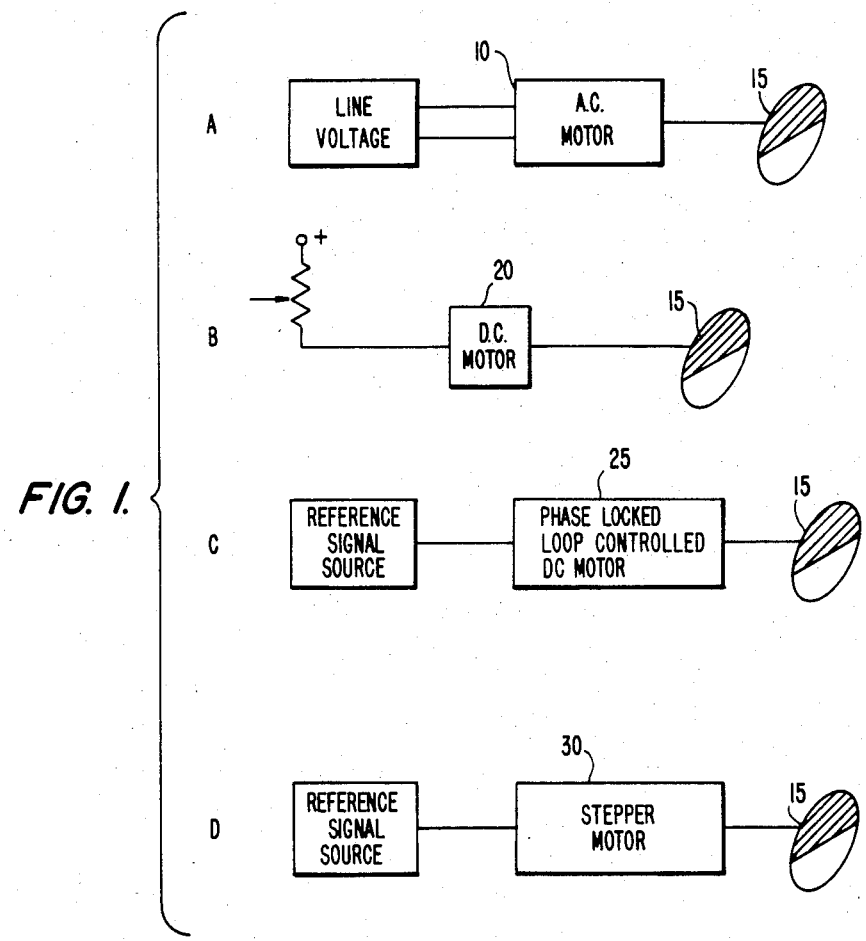
FIG. 1A-1D schematically illustrate previous chopper wheel drive systems developed by the applicant.
Figure 2:
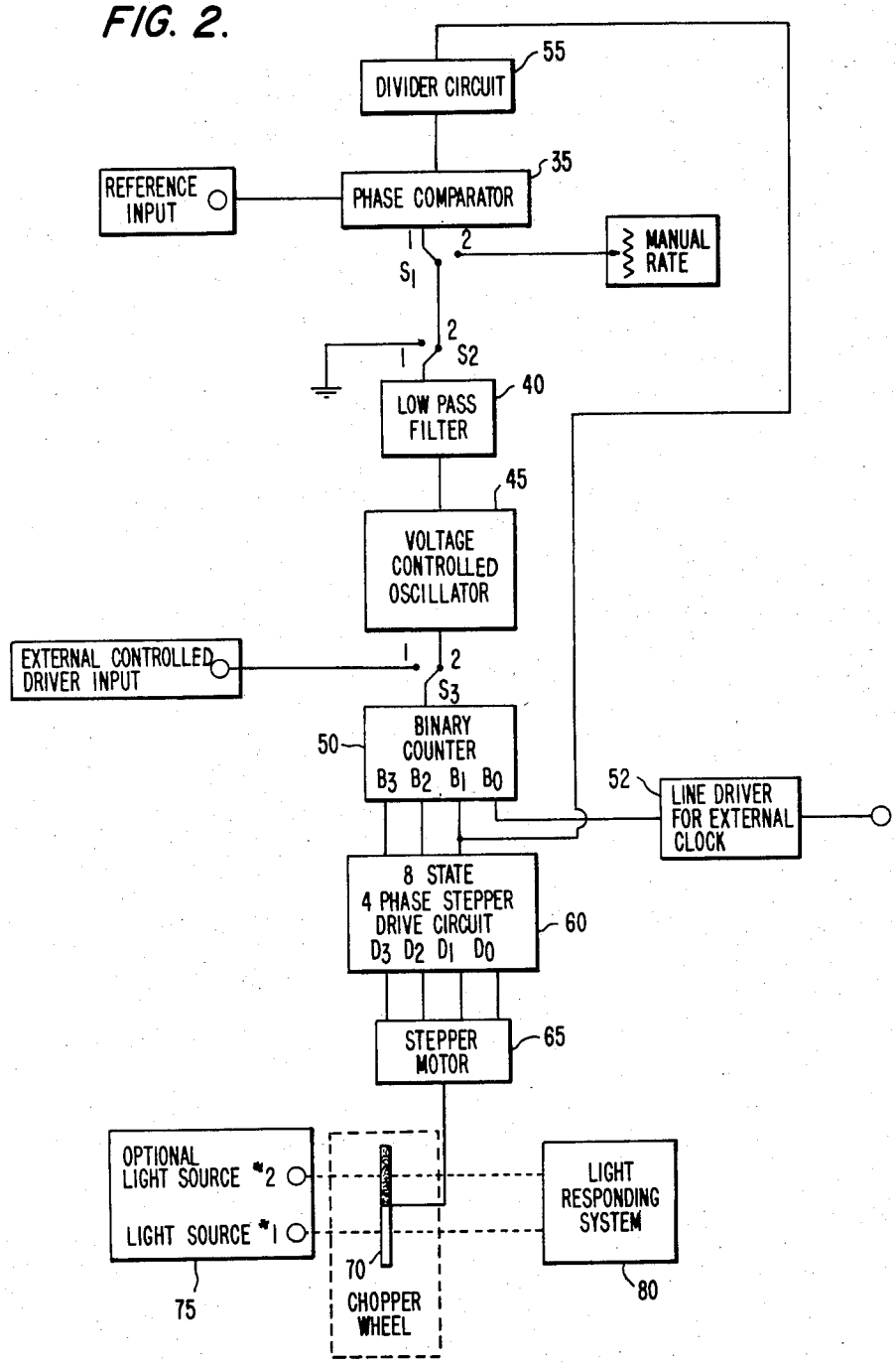
FIG. 2 is a block diagram of a preferred embodiment of a phase locked stepper motor control light chopper according to the present invention.

FIG. 2 is block diagram of the phase locked stepper motor controlled light chopper according to the present invention. In this system, a phase comparator 35 receives a reference input, which in the preferred embodiment is 60 Hz, and compares this signal to a comparison signal. The phase comparator 35 produces a phase signal which in the preferred embodiment has a level corresponding to the phase difference between the reference input and the comparison signal. The phase signal generated by the phase comparator 35 is provided to one of the two inputs of switch S1. The other input to switch S1 is a manual rate input which allows the system to drive a chopper wheel at a manually selected rate rather than at a rate defined by the reference input. As illustrated, S1 is in its first position corresponding to the system operating in a phase locked loop mode.

Low pass filter 40 has at its input, switch S2 which operates as an ON/OFF switch. In position 1 of S2, the system does not drive a chopper wheel, while in position 2 of S2, the signal applied to terminal 2 of S2 (e.g., the phase signal output of the phase comparator 35) is applied to the low pass filter 40. The low pass filter 40 filters the phase signal generated by the phase comparator 35 so that the output voltage of the low pass filter is a slow varying signal.

This slow varying signal controls a voltage controlled oscillator 45 which produces signal pulses having a frequency varying in accordance with the amplitude of the output voltage produced by the low pass filter 40. In the preferred embodiment, the voltage controlled oscillator 45 operates at a frequency of 2.4 KHz when the phase comparator 35 detects that the phase of the reference input corresponds to that of the comparison signal.

Switch S3 provided at the input to binary counter 50 allows the binary counter 50 to be driven by either the signal pulses generated by the voltage controlled oscillator 45 (when S3 is in position 2), or by an external driver input (when S3 is in position 1). As illustrated, the signal pulses generated by the voltage controlled oscillator 45 drive the binary counter 50. In the preferred embodiment, the binary counter 50 has four count signal outputs corresponding to the binary representation of the number of signal pulses counted. The least significant bit of this count, B0, is applied to a line driver for an external clock 52. Because the voltage controlled oscillator 45 produces a 2.4 KHz signal when the phase difference between the reference input and the comparison signal is zero, the external clock has a rate of 1.2 KHz. Similarly, the output B1 of the binary counter 50 has a frequency of 600 Hz and is applied to the input of a divider circuit 55. In the preferred embodiment, the divider circuit 55 divides the frequency of the signal generated at the B1 output of the binary counter 50, by 10. Consequently, when the voltage controlled oscillator 45 oscillates at the rate of 2.4 KHz, the comparison signal has a frequency of 60 Hz which corresponds to the frequency of the reference input in the preferred embodiment.

The three most significant bits of the count signals, B3, B2 and B1 generated by the binary counter 50 are applied to the eight (8) state four (4) phase stepper drive circuit 60. This circuit generates a four (4) phase signal having eight (8) states where each state of the four (4) phase signal is identified by a particular state of the count signals B3, B2, B1.

Figures 4, 5:
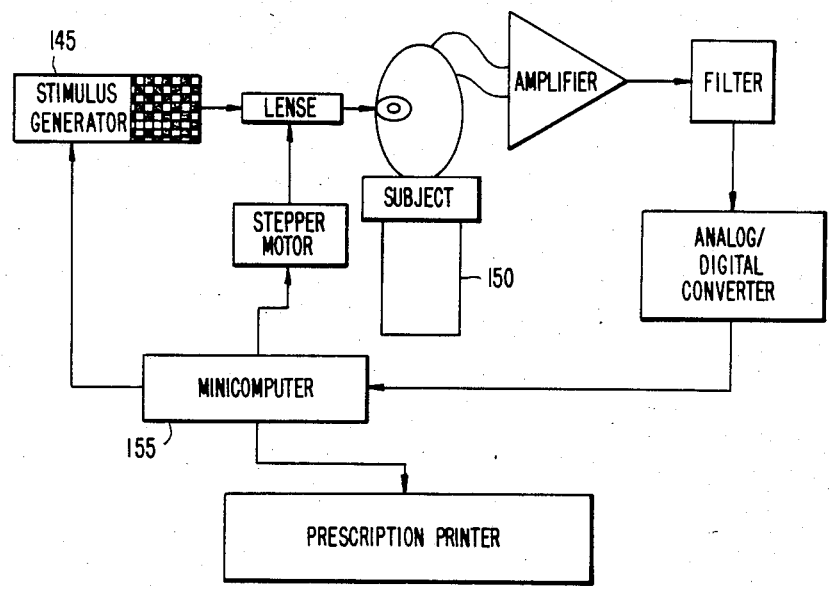
FIG. 4 illustrates a ROM map providing the data for generating an eight (8) step, four (4) phase stepper motor drive signal.
FIG. 5 is a block diagram of an application of the phase locked stepper motor controlled light chopper of the present invention.

FIG. 4 illustrates the correspondence between the state of the count signals, and the particular four (4) phase signal generated by the eight (8) state four (4) phase stepper drive circuit 60. The count signals function as address signals to a memory within the drive circuit 60, while the four (4) phase signals generated by the eight (8) state four (4) phase stepper drive circuit 60 corresponds to the data stored in the memory. As will be recognized by those skilled in the art, the particular correspondence shown in FIG. 4 is merely illustrative and that many other variations are possible. For example, more memory locations could be utilized to repeat the eight (8) states of the four (4) phase signal, and an additional count signal used to distinguish between the first or second sequence of the eight (8) states. Further, the memory could be programmed so that the particular states shown in FIG. 4 were reversed. In such a case, a stepper motor driven by the reversed order data would run in a direction opposite to that defined by the data illustrated in FIG. 4.

The four (4) phase signal generated by the eight (8) state four (4) phase stepper drive circuit 60 is applied to a stepper motor 65. In the preferred embodiment, the stepper motor comprises a SLO-SYN Synchronous/-Stepping Motor, Type M063-F006 manufactured by Superior Electric Company. The stepper motor 65, having a drive shaft 67, drives a chopper wheel 70 so that a pattern printed on the chopper wheel 70 is reversed at the preferred rate of 6 Hz. When the stepper motor 65 drives the chopper wheel 70, light from light source 75 is transmitted to or blocked from a light responding system 80. The light responding system corresponds to for example, a human eye.

Figure 3:
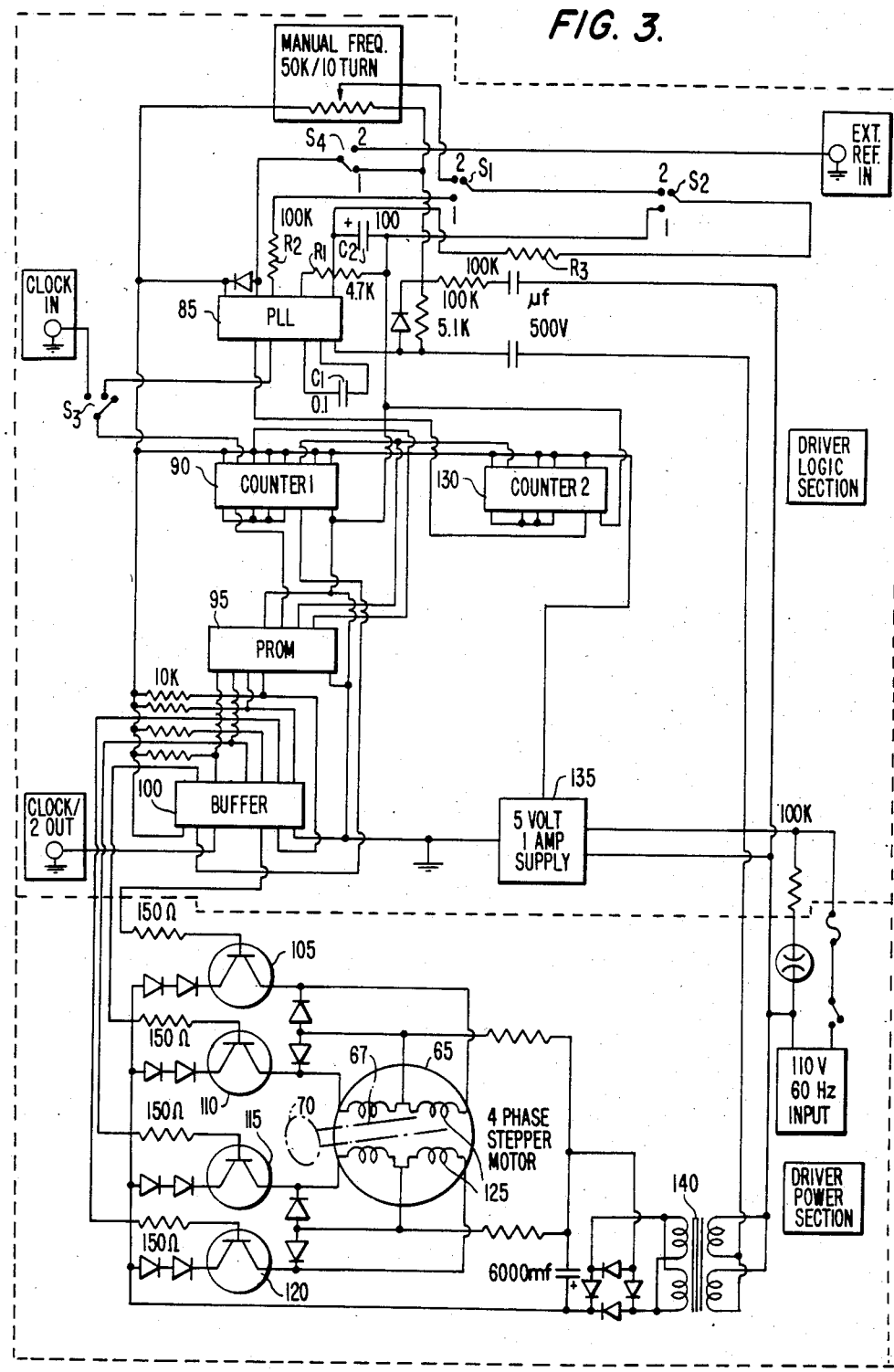
FIG. 3 is a circuit schematic of a preferred embodiment of the system illustrated in FIG. 2.

FIG. 3 is schematic circuit diagram of the phase locked stepper motor control light chopper of the present invention. Switches S1 and S4 determine the input to the phase locked loop (PLL) 85 which can be (1) a manual input if S1 is in position 2, (2) an external reference signal if S4 is in position 2 or (3) a 60 Hz reference signal if S4 is in position 1. Switch S2 determines whether or not the phase locked looped (PLL) 85 rotates the motor 65 (e.g., switch S2 position 2), or holds the motor in a specific position (e.g., switch S2 in position 1). As shown in FIG. 3, the circuit PLL 85 includes the phase comparator 35 and the voltage control oscillator 45 of FIG. 2. The PLL 85 can comprise a CD4046B manufactured by RCA Co. Capacitor C2 and resistor R3 comprise the low pass filter 40 illustrated in FIG. 2.

Switch S3 determines whether or not the output of the voltage controlled oscillator included in the PLL circuit 85 is applied to a first counter, COUNTER1, reference numeral 90, or whether an external clock drives the first counter 90. The first counter 90 can comprise a CD4029 manufactured by RCA Co., and is connected as a binary counter.

In FIG. 3, the first counter 90 produces four (4) outputs having voltage levels correponding to the number of transitions in the output of the PLL 85 or in the clock input if switch S3 is positioned to apply the clock input to the first counter 90.

The most significant three (3) bits of the output of the first counter 90 are applied to the address lines of a programmable read only memory 95 (PROM). PROM 95 can comprise any type memory circuit for example, DM87S188 manufactured by National Semiconductor. The data stored in the PROM 95 corresponds to the particular four (4) phase signal that should be applied to the stepper motor 65. FIG. 4 illustrates the correspondence between the address input to the PROM and the corresponding data stored in the PROM 95. The data stored in the PROM 95 comprises an eight (8) state four (4) bit gray code. The data outputs of the PROM 95 are applied to inputs of a buffer 100. The outputs of the buffer 100 respectively drive the bases of transistors 105, 110, 115 and 120 to a level corresponding to the particular gray code appearing at the output of the PROM 95. The respective collectors of transistors 105, 110, 115 and 120 are connected to the appropriate windings 125 of the stepper motor 65. The transistors can comprise, for example, Darlington power transistors type number MJ2500 manufactured by Motorola Co.

The least significant output bit of the first counter 90 is applied to an input of a second counter COUNTER2 identified by reference number 130 which is connected to count in a base 10 mode rather than the binary mode of the first counter 90. The second counter 130 can comprise a CD4029 manufactured by RCA Co. In this mode, the second counter 130 has a capacity of 10 counts. The carry output of the second counter 130 corresponds to the comparison signal and drives the phase comparator circuit, PLL 85.

The five (5) volt power supply 135 provides the five (5) volts and ground reference required for the logic section of the driver. The five (5) volt power supply 135 can comprise a model number 84-05-210 supply manufactured by SOLA. The transformer 140 provides the power supply voltages required to operate the stepper motor 65. The transformer can comprise, for example, a model 23V52 manufactured by Thoradson Co.

FIG. 5 illustrates one application of the phase locked stepper motor controlled light chopper of the present invention. The subject invention would be included in the stimulus generator 145 to create a reversal pattern for the checker board pattern shown in FIG. 5. The system illustrated in FIG. 5 represents an evoked autorefractometry system that automatically selects the proper lens prescription for a subject 150 by monitoring the brain waves of the subject 150 while viewing the reversing checker board pattern generated by stimulus generator 145. The specifics of the system illustrated in the FIG. 5 are described in the copending and concurrently filed U.S. patent application previously mentioned. In this system, the phase locked stepper motor controlled light chopper of the present invention provides the accurate reversal rate for the checker board pattern generated by the stimulus generator 145. By generating an accurate reversal rate, the microcomputer 155 can detect when the subject 150 best perceives the reversing checker board pattern.

The many features and advantages of the invention are apparent from the detailed specification and, thus, it is intended by the appended claims to cover all such features and advantages of the chopper which fall within the true spirit and scope of the invention. Further, since numerous modifications and changes will readily occur to those skilled in the art, it is not desired to limit the invention to the exact construction and operation illustrated and described; and accordingly, all suitable modifications and equivalents may be resorted to, falling within the scope of the invention.

What is claimed is:

1. A phase locked loop stepper motor controlled light chopper, comprising:
    comparator and signal generation means, operatively connected to receive a reference signal and a comparison signal, for generating signal pulses in accordance with a difference between phases of said reference signal and said comparison signal;
    counter means, operatively connected to receive the signal pulses, for counting the signal pulses and for providing count signals varying in accordance with the counted number of the signal pulses;
    divider means, operatively connected to receive a one of the count signals, for counting a predetermined number of the one of the count signals and for providing the comparison signal each time the predetermined number of count signals is counted;
    driver means for generating a four phase signal having eight states varying in response to the count signals;
    a stepper motor having a drive shaft rotated in response to the four phase signal ; and
    a chopper wheel mounted on and rotated by the drive shaft.

2. A phase locked loop stepper motor controlled light chopper according to claim 1, wherein said comparator and signal generation means comprises:
    phase comparator means, operatively connected to receive said reference signal and said comparison signal, for generating a phase signal varying in accordance with a phase difference between said reference signal and said comparison signal;
    filter means, operatively connected to recieve said phase signal, for filtering said phase signal and for providing an output voltage corresponding to said filtered phase signal; and
    oscillator means, operatively connected to receive said output voltage, for generating said signal pulses having a frequency varying in accordance with said output voltage, and wherein said filter means comprises a low pass RC filter, said counter means comprises a four bit binary counter and said divider means comprises a decimal counter having a carry output corresponding to the comparison signal.

3. A phase locked loop stepper motor controlled light chopper according to claim 2, wherein said driver means includes a memory circuit having an eight state four bit gray code stored therein, wherein the four bits corresponds to the four phase signal applied to said stepper motor.

4. A phase locked loop stepper motor controlled light chopper for providing a specific pattern reversal rate for a pattern in an evoked potential autorefractometry system, comprising:

a phase comparator circuit having a first input operatively connected to receive a reference signal, a second input operatively connected to receive a comparison signal and an output varying in accordance with a phase difference between the reference signal and the comparison signal;

a low pass filter having an output terminal and being operatively connected to the output of the phase comparator circuit;

a voltage controlled oscillator having a control input operatively connected to the output terminal of said low pass filter and a frequency output for providing signal pulses;

a binary counter having a clock input operatively connected to receive the signal pulses and a plurality of count outputs for providing count signals representing a number of signal pulses received;

a counter circuit having a clock input operatively connected to receive a one of the count signals and having an output responsive to a predetermined number of the one of the count signals and corresponding to said comparison signal;

a memory circuit including memory locations for storing an eight state gray code, address inputs operatively connected to receive at least some of the count signals, and data outputs providing the gray code in accordance with the count signals;

a plurality of transistors, each having a base operatively connected to receive a corresponding one of the data outputs, an emitter operatively connected to receive a first supply voltage and a collector;

a stepper motor having a four phase winding operatively connected to respective ones of the collectors and to receive a second supply voltage, and having a drive shaft; and a chopper wheel including the pattern, mounted on and rotated by the drive shaft at a rate for providing the specific pattern reversal rate.

5. A phase locked loop stepper motor controlled light chopper according to claim 4, wherein said counter circuit comprises a decimal counter having an output corresponding to the comparison signal.

6. A phase locked loop stepper motor controlled light chopper according to claim 4, wherein the reference signal has a frequency of 60 Hz.

* * * * *